| United States Patent [19] | [11] Patent Number: | 4,894,348 |
| Ronald Robert C. et al. | [45] Date of Patent: | Jan. 16, 1990 |

[54] FLUORESCEIN-CONJUGATED PROTEINS WITH ENHANCED FLUORESCENCE

[76] Inventors: Ronald Robert C., Rte. #1, Box 844, Pullman, Wash. 99163; Phuc H. Nguyen, 1735 Pine Hollow Cir., San Jose, Calif. 95133; Gerald L. Rowley, 7150 Rainbow Dr., #20, San Jose, Calif. 95129

[21] Appl. No.: 69,288

[22] Filed: Jul. 1, 1987

[51] Int. Cl.$^4$ .......................................... G01N 33/533
[52] U.S. Cl. ................................. 436/546; 436/547; 436/800; 436/805; 436/808; 530/390; 530/802; 549/223; 549/225
[58] Field of Search ............... 436/546, 547, 800, 805, 436/808; 530/390, 802; 549/223, 225

[56] References Cited

U.S. PATENT DOCUMENTS 4,476,229 10/1984 Fino et al. ........................... 436/500
4,588,697 5/1986 Khanna et al. ...................... 436/518

FOREIGN PATENT DOCUMENTS 0110186 6/1984 European Pat. Off. ............ 549/223
0199042 10/1986 European Pat. Off. ............ 549/225
0205005 12/1986 European Pat. Off. .

OTHER PUBLICATIONS

Chen, (1977) Analytical Letters 10(10):787-795.
Franzen et al., (1980) Biochemistry 19:6080-6089.
Ogamo et al., (1982) Carbohydrate Research 105:69-85.
Blatt et al., (1986) Biochim. Biophys. Acta 857:85-94.

*Primary Examiner*—Robert Benson
*Attorney, Agent, or Firm*—Irell & Manella

[57] ABSTRACT

A method for conducting assays for an analyte, usually in a biological sample, utilizes reagents which contain biological ligands linked to fluorescein or a derivative of fluorescein through a linkage to the fluorescein nucleus selected from acetamido and thioacetamido. In these reagents, the fluorescence efficiency is improved over that obtained in the commonly used FITC-labeled reagents.

11 Claims, No Drawings

FLUORESCEIN-CONJUGATED PROTEINS WITH ENHANCED FLUORESCENCE

TECHNICAL FIELD

The invention relates to labeling biological materials, in particular, to the labeling of proteins. Specifically, derivatized fluoresceins are prepared which permit formation of conjugates of fluorescein with protein or other biological molecules having fluorescence intensities higher than those obtained using standard fluorescein isocyanate (FITC) labeling, for use in immunological assays.

BACKGROUND ART

Fluorescein is a commonly used labeling material for protein, in particular in the context of immunoassays. Immunoglobulins can be readily made detectable by conjugation to fluorescein.

Typically, this conjugation is effected by reacting commercially available fluorescein isothiocyanate (FITC) with the compound to be labeled. This results in a thiourea linkage involving the isothiocyanate of FITC and free amino groups on the protein. The resulting thiourea-linked fluorescein has diminished fluorescence as compared to fluorescein itself. The corresponding urea derivatives, which would be the products of the analogous reaction of the amino groups of the proteins with fluorescein isocyanate, have higher fluorescence intensities, but have not been used routinely because the starting material, fluorescein isocyanate, is unstable and thus must be freshly prepared before use. Nairn, R. C., "Fluorescent Protein Tracing", 4th ed. (1976), Churchill-Livingston, NY, p. 17.

It has now been shown that replacing the thioureido group with a thioacetamido, or, preferably, acetamido, subunit enhances the ability of the resulting compound to fluoresce. Accordingly, compounds have been designed which contain the configuration —NHCSCR$_2$—, or preferably —NHCOCR$_2$—, in the region immediately adjacent the fluorescein nucleus.

Others have used fluorescein linkages not derived from FITC. For example, Wang, C. H. J., et al, Canadian patent 1,178,269, discloses a method for determining ligands in a sample using labeled compounds wherein a carbonyl group rather than the isothiocyanate residue is directly attached to the fluorescein moiety. Thus, these ligands are directly bound to 4- or 5-carboxyfluorescein. They are formed in a procedure whereby the carboxy group has been activated to permit binding to the desired ligand. According to the reference, these compounds were used to prepare "tracers" for a fluorescence polarization assay, and there is no discussion of the fluorescence efficiency of the conjugates. The disclosure in this reference also refers to the use of carboxyfluorescein by others in forms not conjugated to biological molecules (Chen, R. F., *Anal Let* (1977) 10: 787).

A paper by Franzen, J. S., et al, *Biochemistry* (1980) 19: 6080-6089, refers to the reaction of 5-iodoacetamidofluorescein (and the corresponding eosin) with an enzyme previously labeled with 5-[(iodoacetamido)ethyl)amino]naphthalene-1-sulfonic acid. No special fluorescence intensity properties of these compounds are reported; the donor/receptor relationship of the fluorophores was used to study the locations of the catalytic sites.

It should be noted that compounds derived from fluorescein that contain a halide immediately adjacent the methylene group in the —NHCOCH$_2$— side chains of the invention are commercially available; one such compound, mentioned above, is 5-iodoacetamidofluorescein. In addition, 5-acetamidofluorescein is known to fluoresce at an intensity comparable to that of fluorescein per se. Derivatives of oxidized sugars containing the amide linkage also fluoresce at high intensity levels. These labeled sugars can be then tracked metabolically (Ogano, H., et al, *Carbohydrate Res* (1982) 105: 69-85).

Also, derivatives of steroids using an acetamide type linkage of fluorescein with steroids have been prepared. Four such compounds have CA registry numbers 92264-85-2, 92264-86-3, 93800-97-6 and 61925-79-9; they are evidently prepared by condensation of a steroid-linked carboxyl group with fluoresceinamine. A derivative of the amino derivative of eosin with a fatty acid is also described (Blatt, E., et al, *Biochim Biophys Acta* (1986) 857: 85-94).

DISCLOSURE OF THE INVENTION

Derivatized fluorescein and related fluorophores conjugated to a material to be labeled through an amide linkage in reverse order to that formed in compounds derived from carboxyfluorescein exhibits fluorescence efficiency greater than conventional derivatives of FITC. The fluorescein may be conjugated through this linkage to label a wide variety of materials, including proteins, sugars, steroids, and other biological substances for use in analytical procedures. The essential elements of the linkage are —NHCSCR$_2$—, or preferably —NHCOCR$_2$—, wherein each R is H, or lower alkyl (1-4C), wherein this group is located at position 4 or 5 of the benzoic acid-derived ring of the fluorescein or its substituted derivative. The groups attached to the methylene or alkylated methylene of the acetamido or thioacetamido group provide means to link the fluorescent nucleus to a biological ligand, and may further contain linkages which are specifically cleavable, an advantage possessed by the improved assays described in U.S. Ser. No. 847,505, filed 3 Apr. 1986, assigned to the same assignee and incorporated herein by reference.

In major aspect, the invention is directed to a method to conduct assays for the presence of or amount of a particular analyte, wherein the assay employs fluorescent-labeled reagents containing a biological ligand, and possibly including a linking sequence, labeled with fluorescein or a substituted fluorescein of the formula:

Fl—NHCZCR$_2$— wherein Fl represents a fluorescein residue or a substituted fluorescein residue, such as eosin, Z is O or S, and each R is H or lower alkyl (1-4C). It is believed that the embodiments wherein Z represents O are superior in fluorescence efficiency. Assays conducted with the use of labeled reagents wherein the fluorescent label is of the formula set forth above are more sensitive than conventional assays, due to the increased fluorescence efficiency of the labeled reagent. The biological ligand labeled is preferably an immunoglobulin or derivative thereof, but can be chosen from a wide range of materials.

The invention is also directed to kits for conducting assays using the above-mentioned reagent.

In addition, the invention is directed to compounds useful in preparing the labeled reagents useful in the method of the invention of the formula:

$$Fl-NHCZCR_2-X-L \quad (1)$$

wherein

Z is O or S, each R is H or lower alkyl (1-4C),

X is optionally substituted $(CH_2)_n$ wherein n is 0-10 and wherein one of the $CH_2$ units may be replaced by O or NR (R=H or lower alkyl), or one or two of the $CH_2$ units may be replaced by S; and wherein L is a functional group capable of forming a covalent bond to a desired biological ligand or to a linker.

In another aspect, the invention is directed to compounds derived by reaction of the compounds of formula 1 with biological ligands or linked ligands, these compounds having the formula:

$$Fl-NHCZCR_2-X-L'-Y' \quad (2)$$

wherein Fl, X, R, and Z are as above defined.

In the compounds of formula 2, L' is a residue of L as above defined, but modified by conjugation to Y', Y' is the residual form of the desired biological ligand (or biological ligand conjugated to linker), Y, modified by virtue of its conjugation to the fluorescein derivative. Y itself may be protein, carbohydrate, low molecular weight cofactor, or any of these bound to linker.

MODES OF CARRYING OUT THE INVENTION

The Assays

In the method of the invention, the fluorescent-labeled reagents containing the required form of conjugation are useful in a variety of contexts. For example, in circumstances wherein the biological ligand is a residue of the analyte, the reagent is useful in competitive assays for these analytes. In instances where the biological ligand is derived from an antibody or fragment thereof, these reagents are useful in the conduct of immunoassays using a variety of protocols well known in the art.

Thus, in general, the assays to which the labeled reagents are applicable are conducted either in a direct or competitive manner. In direct assay, the specific reagent is either itself labeled, or provided a mechanism to acquire the label, and used to bind to the analyte in the sample, thus removing it from the physical environment of the contaminants, or in some way changing the environment so that only the analyte's presence among the associated materials in the mixture is detectable. The amount of label associated with the analyte is then a direct measure of the quantity of analyte in the sample. Often a labeled antibody is employed for direct assays, in which case the assay is general termed "immunometric". The fluorescence efficiency provided in the methods of the invention which employ the required manner of linking label to substrate permits increased sensitivity in this type of assay by conferring a higher order of fluorescence on the separated, labeled, complex of analyte with the labeled reagent as compared with conventional techniques.

For use in direct assays, therefore, the fluorescent-labeled reagents contain the fluorescein or derivative directly conjugated to a reagent specifically reactive with analyte either directly (when label is attached to the primary antibody) or through an intermediate link, such as a different antibody, i.e., the analyte reacts either with a primary antibody which contains label, or the primary antibody may be unlabeled, but then reacted with a secondary labeled antibody. In the labeled reagents of formula 2, the Y' residue of these compounds may be derived from suitable immunoglobulins. For example, Y', or, in general, the biological ligand, may be the reaction product residue derived from rabbit anti-mouse antibody preparations, which then can be used to label a specifically binding murine antibody specific for any of a wide variety of analytes, such as various drugs and other biologically important substances. In the alternative, the biological ligand could be a monoclonal antibody specific for the analyte of choice, for example ferredoxin, and a second unlabeled antibody specific for ferredoxin bound to a solid support is used to complete the sandwich of a different, but standard, assay format.

Conversely, in the competitive approach, the analyte is caused to compete with itself in labeled form for the same specific reagent. The higher the concentration of competing analyte in solution, the less label will be bound to the specific reagent. Thus, the amount of label associated with the specific reagent/analyte complex is in inverse proportion to the amount of analyte in solution. For use in this type of assay, the biological ligand is the analyte itself.

Typical analytes for use in this and the direct reaction format are so many and varied as to defy listing, but would include, for example, prostaglandins, antiasthmatic drugs, steroids, antibiotics, substances which are abused such as morphine and heroin, antidepressant drugs, antiinflammatory drugs, various proteins such as enzymes, hormones, structural proteins, and lymphokines, saccharides, such as those associated with various blood groups, and so forth. The labeling method of the invention and the reagents provided for performance of this method are broadly applicable to the determination of any analyte in a range of standard procedures.

The assay protocols involving labeled reagents can also be applied to histological sections or cytological smears. In these embodiments, for example, an immunoglobulin labeled according to the invention may be used to stain the solid section of samples suspected to contain the antigen to be measured. Alternatively, a labeled antibody fragment of other specific binding partner can be used.

In general, the methods and materials of the invention are employed in ways completely analogous to those previously practiced in the art by derivatization of a general substrate (e.g., biological ligand) using FITC. Thus, alternate affinity-based assays, such as those involving receptor-ligand binding, will also employ these reagents and are within the scope of the invention.

The materials for the assays may be packaged into kits in suitable containers and in convenient packaging arrangements, along with instructions for performing the assay.

The Fluorescent Label

The fluorescein nucleus contained in the compounds of the invention has the formula:

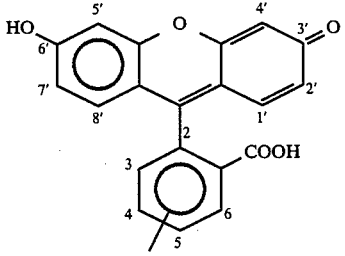

(3)

wherein the attachment of a conjugated functional group or biological ligand is at position 4 or 5 of the benzoic acid-derived ring. When placed in alkali, the compound becomes fluorescent, and the fluorescent form of the compound is a dianion of the formula:

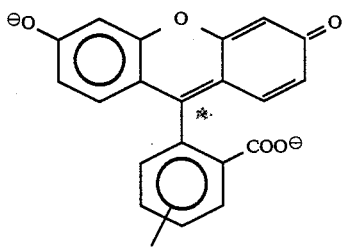

(4)

Accordingly, the compounds useful in the invention, all of which contain this nucleus, include those in any status of ionization, since by adjustment of pH of the surroundings, the fluorescent form may be obtained. Thus, included within the scope of the invention are the free-acid form, the monoanion, and the dianion, and the salts of the latter two. These salts may be formed from inorganic ions such as potassium, sodium, ammonium, and the like, or organic moieties such as caffeine or other amines. Of course, the soluble inorganic salts are most convenient.

Also included within the fluorescein compounds useful in the invention are derivatives wherein substitutions have been made on the basic fluorescein nucleus. Perhaps the best known of these include the eosin derivatives; for example, eosin-1 bluish, which is the fluorescein nucleus substituted with bromo substituents in the 4' and 5' position and with nitro substituents in the 2' and 7' positions; eosin yellowish contains bromo groups in all four of these positions. The color of fluorescence can be altered by substitution of groups with the appropriate electron-withdrawing or electron-donating abilities in these positions of the basic fluorescein nucleus.

Forms of fluorescein or its substituted derivatives containing additional functional groups at positions 4 and 5 are commercially available and are important intermediates. Particularly useful in the preparation of the compounds of the invention are the 4- and 5-substituted fluoresceins containing iodoacetamido at one of these positions. Intermediates can also be made using fluoresceinamine—i.e., fluorescein having a free amino group at one of positions 4 or 5. For convenience in notation, the fluorescein (or substituted derivative) residue conjugated at position 4 or 5 will be represented as (4-Fl)- or (5-Fl)- or, generally Fl—.

Reagents and Intermediates

In addition to the methods of the invention which are characterized in their employing fluorescent-labeled reagents wherein the fluorescent label is represented by Fl—NHCZCR$_2$—, the invention includes compounds useful in the preparation of these fluorescent-labeled reagents and some of the resulting reagents themselves. Thus, the invention also includes compounds of the formulas 1 and 2 as set forth above, wherein the —NHCZCR$_2$— moiety is at position 4 or 5 of the fluorescein or fluorescein derivative.

In the methylene or substituted methylene adjacent CZ, each R can independently be H or lower alkyl (1-4C). Lower alkyl may include, therefore, methyl, ethyl, i-propyl, i-butyl and so forth.

For compounds of the invention herein, useful in preparing the desired fluorescent-labeled reagents, the NHCZCR$_2$— bridge is, in turn, covalently bound to the substituent —X—L. These compounds are used to conjugate to the biological material or linked biological material of interest, so as to obtain the desired reagents.

Reagents comprising compounds of the invention have the formula Fl—NHCZCR$_2$—X—L'—Y', wherein Y' represents the derivatized form of the biological ligand of interest. The notation L' and Y' is used because it is recognized that in the process of conjugation, substituents of L and Y may be lost. Typically, water is split out in the process of forming conveniently obtained linkages.

Typically, the biological ligand in the reagents used in the method of the invention is a protein, and most usually an immunoglobulin or fragment such as an Fab, Fab' or F(ab')$_2$ fragment thereof, or other fragment which retains the immunospecificity of the antibody. Other specifically reacting proteins, such as biotin, are also useful. As with other biological materials, the protein may be conjugated to a linker and in the resulting compound Fl—NHCZCR$_2$—X—L'—Y' the Y' residual also contains the residue of the linker. Other biological ligands include steroids (when n is at least 2), sugars, fatty acids, enzymes, glycoproteins, or any molecule of interest.

Typical embodiments of L include carboxyl, sulfhydryl, amino groups, halomethyl, and so forth. Also included, of course, are other easily linked functional groups such as epoxides, aldehydes, alcohols, derivatized carboxyls, or vinyl and the like. Depending on the nature of L, the atoms resulting in L' may be the same as or less than in the original compound.

The choice of the functional group represented by L will depend on the functional group available on the substance to be labeled, Y. For example, if Y contains a conveniently available hydroxyl group, a carboxyl or activated carboxyl group may be convenient for L. Similarly, if Y contains an amine it may be advantageous to choose an activated carboxyl or an aldehyde for L. In either case, an epoxide group would also be applicable. L might, in some instances, be halomethyl, such as —CH$_2$Cl, provided the Y group contains a substituent sufficiently nucleophilic to displace it. A particularly favored embodiment of L is —SH, which is reactive, for example, with ligands conjugated to commonly used linkers containing a maleimide residue. The various compatible embodiments of L with the particular substituents available in Y will be clear to those of ordinary skill in the art.

X is represented by the formula —(CH$_2$)$_n$—, wherein n has a value of 0-10, preferably 2-6, and most preferably 3-6. When L is COOH, n must be at least 2. One or two of the CH$_2$ units may be replaced by S, or one of them may be replaced by O or NR wherein R is lower alkyl (1–4C). In a particularly useful embodiment, two adjacent CH₂ groups are replaced by S—S, thus providing a readily cleavable linkage, as referenced in U.S. Ser. No. 847,505 (supra).

The methylene or heteroatom-containing chain represented by X may also contain functional groups which do not interfere with the function of the finished reagent or with its synthesis. A requirement for such functional groups is that they be unreactive with either L or Y under conditions wherein L or Y react to form the finished reagent. Thus, if L is represented by SH and Y contains maleimide as the reactive functional group, the presence of, for example, hydroxyl groups could be tolerated in X. X may also be substituted by hydrocarbyl side chains which clearly are unreactive under the conditions employed.

The biological compounds of interest may be previously linked to linker reagents to facilitate their conjugation to the intermediate compounds of the invention. Thus, the residue designated by Y' may include the linker as well as the biological ligand. In particular, proteins or other biological materials may be reacted with the commercially available linkers such as succinimidyl 4-(N-maleimidomethyl) cyclohexane-1-carboxylate (SMCC) or succinimidyl 4-(4-N-maleimidophenyl) butyrate (SMPB) of their solubilized forms, such as their sulfo forms, which contain activated carboxyls for reaction with amines included in the ligand to provide the maleimide-derivatized materials. The maleimide provided by the linker then readily reacts with a sulfhydryl embodiment of L to obtain a thioether.

Besides use of the compounds of formula 1,5-iodoacetamidofluorescein may be used as a starting material; this starting material will react with a CH₂SH-containing compound, including a biological ligand, to provide a CH₂—S—CH₂ linkage.

Alternatively, fluoresceinamine can be used as a starting material and reacted with an activated form of carboxylic acid to obtain the corresponding amide. Illustrative but not limiting examples are provided to show these particular syntheses.

Synthesis Methods

In general, methods to obtain the appropriately substituted fluorescein or derivative are within the skill of the art.

In one useful approach, 4- or 5-iodoacetamidofluorescein is used as starting material and reacted with a corresponding "X-L" containing a mercaptan or alcohol, according to the scheme:

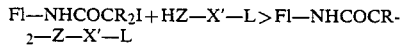

Fl—NHCOCR₂I + HZ—X'—L > Fl—NHCOCR₂—Z—X'—L (X' is used here, because X as above-defined would be (Z—X').) When Z is O, the reaction takes place under basic conditions; when Z is S, reaction takes place at neutral pH. The reaction takes place at a temperature of 0° to 100° C. in a polar solvent, including aqueous polar solvents.

In an alternative approach, the compounds of formula 1 are obtained according to the scheme:

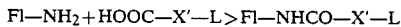

Fl—NH₂ + HOOC—X'—L > Fl—NHCO—X'—L wherein the condensation to form the amide takes place in the presence of a dehydration agent such as dicyclohexylcarbodiimide (DCC) or ethyldiimide under suitable conditions.

As stated above, the iodoacetamido fluorescein or derivative and the fluorescein or related fluorophore amine can also be reacted directly with the desired biological ligand or linked ligand to obtain reagents useful in the invention.

EXAMPLES

The following examples are intended to illustrate, but not limit, the invention.

EXAMPLE 1

Preparation of 5-((((2-carboxyethyl)thio)acetyl)amino)fluorescein (5-Fl)—NHCOCH₂SCH₂CH₂COOH (Fluorescein I)

3-Mercaptopropionic acid, 80 µl, was dissolved in a mixture of 6 ml DMF and 3 ml of 50 mM phosphate, 2.5 mM EDTA, pH 6.30, buffer. Tris (hydroxymethyl)aminomethane, 200 µl, 1.5M, pH 8.8 (Tris buffer) was added to adjust the pH of the mixture to 6.30. A solution of 5-iodoacetamidofluorescein, 200 mg, dissolved in 7 ml of dimethylformamide (DMF), and 4 ml of 50 mM phosphate, 2.5 mM ethylenediamine tetracetic disodium salt (EDTA), pH 6.30 buffer, was added slowly with stirring. Tris buffer, 50 µl, was added to bring the pH to 6.2. The resulting solution was heated in a 50° C. water bath overnight.

Thin-layer chromatography, ethylacetate:acetic acid (25:1, v/v), was used to monitor the reaction. When the reaction was greater than 90% complete, 86 ml of deionized water and 100 µl of 10% HCl were added to adjust the pH to 3.2. The mixture was stirred for 3 hr at room temperature, then stored at 4° C. overnight to yield an orange precipitate. The precipitate was collected by centrifugation and washed three times with 12 ml portions of deionized water that was acidified with 1 µl of 10% HCl, using centrifugation between each wash (3 ml each into 4 tubes).

The pellet were dissolved in a solution of 8 ml of methanol and 300 µl of Tris buffer and isolated by preparative thin-layer chromatography (TLC) on silica, ethylacetate:acetic acid (25:0.075, v/v). The product was removed from the silica with 200 ml of the above solvent and the solvent removed under reduced pressure. The resulting orange solid was triturated with dichloromethane six times to remove acetic acid. The solid was then dissolved in 3 ml methanol and 80 µl Tris buffer, then purified once more by preparative TLC. After removal of solvents under reduced pressure, the product was dried in vacuo overnight (P₂O₅, 60° C.). Anal calc. for C₂₅H₁₉O₈NS.H₂O: C, 58.69%; H, 4.10%; N, 2.74%; S, 6.27%. Found C, 58.67%; H, 4.18%; N, 2.71%; S, 6.13%. Molar extinction coefficient: $\epsilon = 78,000$ M$^{-1}$cm$^{-1}$ ($\lambda$max=493 nm) in 0.5M sodium carbonate, pH 9.5.

The reactive carboxyl group in the ω position may be further activated for derivatization to desired sample. Thus, for example, carboxyl groups may be converted to "active esters", such as the N-hydroxysuccinimide esters, or may be activated to the corresponding acyl halides.

EXAMPLE 2

Preparation of N-Hydroxysuccinimide Ester of Fluorescein I (5-Fl)—NHCOCH$_2$SCH$_2$CH$_2$CONHS A 50 μl portion of a solution of 3.45 mg N-hydroxysuccinimide (NHS) and 4.22 mg of 1-(3-dimethylaminopropyl)-3-ethylcarbodiimide hydrochloride in 400 μl anhydrous dimethylformamide (DMF) was added to 1.28 mg fluorescein I in 50 μl of anhydrous DMF. The solution was stored at room temperature. Formation of NHS ester of fluorescein I was monitored by thin-layer chromatography (TLC); ethyl acetate:acetic acid (25:1 v/v). Reaction was found to be greater than 80% complete by TLC after 7 hr. The resulting solution was used to label rabbit Fab'.

EXAMPLE 3

Preparation of Fluorescein I-Labeled Fab' Fragments

The fluorescein I compounds, suitably activated in the ω position, may be used to label desired biological substrates. In this example, the activated fluorescein I prepared in Example 2 is used to obtain labeled Fab' fragments.

Rabbit F(ab')$_2$, available commercially or readily synthesized from rabbit IgG using pepsin digestion, was first converted to Fab' by treating with reducing agent. A 32 μl portion of 1.1M cysteamine hydrochloride solution was added in three equal portions to 3.2 ml of a solution containing 40 mg rabbit F(ab')$_2$ in 100 mM sodium phosphate, 5 mM EDTA, pH 6.0, with stirring over a 3 min period. The resulting clear solution was incubated at 37° C. for 30 min and then dialyzed for 2 days against 5×100 ml buffer changes at 4° C. Fab' thiol group, 0.99 per mole, was titrated with 5,5'-dithiobis(2-nitrobenzoic acid).

A portion of the NHS ester of fluorescein I in DMF, 92 μl, was slowly added to 1.40 ml of 1.92×10$^{-4}$M Fab' with stirring in an ice-water bath under argon. After last addition, the resulting yellow-orange solution was incubated at room temperature for six hours under argon. Hydroxylamine hydrochloride, 3.0M, 5 mM EDTA, pH 6.0, 0.50 ml, was added slowly with stirring in an ice-water bath, then the mixture was incubated for one hour at room temperature. The resulting solution was loaded onto a 12.5 cm×1.0 cm G-25 Sephadex column and eluted with 50 mM phosphate, 5 mM EDTA, pH 6.0, buffer. The peak fractions of labeled protein were pooled. The resulting labeled Fab' fragments were found to contain 1.9 fluoresceins per mole by ultraviolet spectroscopy. Titration of Fab' thiol moiety with 5,5'-dithiobis(2-nitrobenzoic acid) indicated 0.40 thiols per mole.

EXAMPLE 4

Use of Conjugated Fluorescein I as Label

The Fab' fragments labeled with fluorescein I could then be conjugated to an additional protein, in this example, α-fetoprotein (AFP), through use of a commercially available cross-linker. Initially, the human α-fetoprotein is bound to sulfo-SMCC, commercially available from Pierce Chemical Company, through the activated carboxyl group of the linker. The cross-linker-bound AFP was then conjugated by reaction with the maleimide portion of the linker to the single sulfhydryl group available in the Fab' fragments fluoresceinated with fluorescein I.

Preparation of α-Fetoprotein with a Multiplicity of SMCC Linker

Human α-fetoprotein (AFP), 1.0 mg, was dissolved in 0.5 ml water and dialyzed versus three changes of 100 mM sodium phosphate, 5 mM EDTA, pH 7.0, buffer (300 ml each).

Cross-linker-bound AFP (SMCC-AFP) was prepared by addition of sulfosuccinimidyl 4-(N-maleimidomethyl) cyclohexane-1-carboxylate (sulfo-SMCC) to AFP. Thus, sulfo-SMCC (15 mg/ml in DMF), 18.4 μl, was added to the above dialyzed AFP solution, 0.46 ml, at 0° C. over a 30 min period. The reaction mixture was warmed to 30° C. and incubated for 120 min.

SMCC-AFP was separated from unbound sulfo-SMCC by gel filtration on a prewashed Sephadex G-25 column (1.0×19 cm) in 100 mM sodium phosphate, 5 mM EDTA, pH 6.0. After elution, the protein peak was determined by measurement of the optical absorbance of fractions at 278 nm. The peak fractions were pooled and used for preparation of fluorescent-labeled AFP reagent.

The incorporation of SMCC into AFP, 4.2 per mole, was measured by reaction with an excess of a standardized solution of 2-mercaptoethanol followed by determination of unreacted 2-mercaptoethanol with 5,5'-dithiobis(2-nitrobenzoic acid).

Preparation of Labeled α-Fetoprotein Reagent

Fab' fluoresceinated with fluorescein I (Fl'-Fab') was added to the SMCC-AFP to incorporate the fluorescein-labeled Fab' into AFP. Fl'-Fab' would be expected to bind only to the AFP-bound SMCC linkers. Based on the bound cross-linker concentration measured in the post-G-25 pool, a 2.26-fold molar excess of Fl'-Fab' was added to SMCC-AFP and the reaction allowed to run for 5 days at room temperature.

The Fl'-Fab' complex was separated from unbound Fl'-Fab' and unreacted SMCC-AFP by gel filtration on a prewashed Ultrogel AcA 44 column (1.5×48.3 cm) in 100 mM sodium phosphate, 5 mM EDTA, pH 6.0, buffer. The Fl'-Fab' complex was slowly eluted overnight and the column fractions analyzed for optical absorbance (278 nm), protein concentration, solution fluorescence, and AFP activity (by RIA). Fractions containing Fl'-Fab' were pooled and used without further purification.

The amount of Fl'-Fab' incorporated into Fl'-Fab' was determined by comparison of the fluorescent output of the Fl'-Fab' with the known fluorescent output of the Fl'-Fab' starting material. It was found that approximately 3.0 Fl'-Fab' per mole were incorporated into the final Fl'-Fab' product.

EXAMPLE 5

Determination of α-Fetoprotein

A manual batch procedure was conducted to determine α-fetoprotein using 20 to 600 ng/ml calibration standards.

Patient serum samples and calibrators, 20 μl each, were dispensed into tubes followed by 100 μl assay buffer wash using a Pipettor-Dilutor. Fluorescent α-fetoprotein reagent (1:200 dilution), 10 μl, was dispensed into the tubes followed by 50 μl of assay buffer.

The tubes were vortex mixed and then goat anti-α fetoprotein antibody (8.5:100,000 dilution), 10 μl, was dispensed into the tubes followed by 50 μl assay buffer wash. The tubes were vortex mixed, then incubated at 37° C. for 2.5 hr. Rabbit anti-goat Ig antibody (6:10 dilution), 10 μl, was dispensed into the tubes followed by 50 μl assay buffer wash. Polyethylene glycol solution (3.2%), 500 μl, was dispensed into the tubes followed by vortex mixing and incubating for 30 min at room temperature. The tubes were centrifuged for 30 min to pellet the immune precipitate. The supernatant was decanted and measurement buffer, 566 μl, was added to dissolve the pellet and the tubes vortex mixed. The resulting solutions were aspirated into the flow cell of the IMMPULSE fluorometer and read.

A standard curve is calculated from the relative fluorescence intensities of the calibrators. The patient sample results are determined by comparison of their fluorescence values to the standard curve.

EXAMPLE 6

Preparation of Cleavable Fluorescein Linker
(5-Fl)—NHCOCH$_2$SSCH$_2$COOH (Fluorescein II)

An additional embodiment designated fluorescein II, which contains a cleavable disulfide linker, was also prepared: 5-((carboxymethyldithiol)acetyl) aminofluorescein or (5-Fl)—NHCOCH$_2$SSCH$_2$COOH.

To a solution of fluoresceinamine (Isomer 1, Aldrich) (100 mg, 0.288 mmole) and dithiodiglycolic acid (1.00 g, 5.5 mmole) in THF (distilled from benzophenone-sodium ketyl) was added with stirring DCC (150 mg, 0.73 mmole) in two portions over a 30 min period. After 30 min the reaction mixture was filtered into Et$_2$O (100 ml). The ether solution was washed with water (5×10 ml), brine, dried with anhydrous Na$_2$SO$_4$, and concentrated at reduced pressure. The crude material was taken up in acetone (2–5 ml) and the DCU allowed to crystallize. The mixture was filtered into a small flask which was put into a jar containing CH$_2$Cl$_2$ so that diffusion of the CH$_2$Cl$_2$ vapor caused slow precipitation of the amide. This afforded a crude product (152 mg) contaminated with unreacted dithiodiglycolic acid. The crystallization was repeated using 2-butanone to afford 108 mg.

This material was chromatographed in silica gel 60 [40–60μ] (50 g) eluted with 1% HOAc-15%MeOH-CH$_2$Cl$_2$ to afford 101 mg (69%) of material judged to be homogeneous by TLC and $^1$H NMR.

EXAMPLE 7

Preparation of

N-Hydroxysuccinimide Ester of Fluorescein II (5-Fl)—NHCOCH$_2$SSCH$_2$CO NHS

To a solution of fluorescein dithiodiglycolmonoamide, fluorescein II, (35 mg, 0.0685 mmole) and N-hydroxysuccinimide (10 mg, 0.087 mmole) in dry acetone (2 ml) was added DCC (20 mg, 0.097 mmole). After 1 h the mixture was filtered into Et$_2$O, washed with water 2X, brine, dried with Na$_2$SO$_4$, and concentrated to an orange oil. By TLC (20% iPrOH—CHCl$_2$) this material appeared to be quite pure, but showed streaking due to decomposition on the plate. The crude oil was dissolved in 2-butanone (1–2 ml) and allowed to crystallize overnight by diffusion of CH$_2$Cl$_2$ to afford 16 mg of orange microcrystals. By TLC and $^1$H NMR this material was judged to be homogeneous.

EXAMPLE 8

Relative Fluorescence of Labeled Fab' Fragments

A comparison of relative fluorescence intensities of rabbit Fab' fragments labeled with either fluorescein-5-isothiocyanate (FITC) or fluorescein I is shown in Table 1. Four conjugates of each fluorophore were prepared with different fluorescein-to-protein ratios (n). Fluorescent light output from Fab' conjugates of I is about 1.8 times the light output from Fab' conjugates of FITC when conjugates of equal levels of fluorophore labeling are compared. Relative fluorescence intensities were determined by making solutions containing $1 \times 10^{-10}$M fluorophore of either rabbit Fab' labeled with FITC or rabbit Fab' labeled with I. Fluorescence was read on a standard IMMPULSE fluorometer (Sclavo Inc. West Coast, Sunnyvale, CA) and compared to the fluorescence output of $1.0 \times 10^{-10}$M fluorescein, which was given an arbitrary value of 1.0.

TABLE 1

| Comparison of Relative Fluorescence of Labeled Rabbit Fab' Fragments | | | |
|---|---|---|---|
| Fab' Fragments Labeled with FITC ((FITC)$_n$-Fab') | | Fab' Fragments Labeled with I ((I)$_n$-Fab') | |
| n | Rel. Fluorescence | n | Rel. Fluorescence |
| 1.0 | 0.44 | 1.0 | 0.77 |
| 2.1 | 0.41 | 2.0 | 0.68 |
| 3.2 | 0.36 | 2.8 | 0.65 |
| 3.8 | 0.32 | 3.8 | 0.58 |

In addition, fluorescein I, itself, as compared to the fluorescence of fluorescein, yielded a relative fluorescence of 0.93; fluorescein II yielded a relative fluorescence of 0.80. These are in comparison with, for example, FITC-labeled glycine t-butyl ester, which has a relative fluorescence of only 0.45.

EXAMPLE 9

Preparation of 5-(2-(Thioacetyl)acetamido)fluorescein (5-Fl)—NHCOCH$_2$SCOCH$_3$ In a 25 ml round-bottomed flask, 5-(iodoacetamido)-fluorescein (113 mg, 220 μmoles) and potassium thioacetate (25.9 mg, 227 μmoles) were combined with methanol (8 ml). The heterogeneous mixture was heated at reflux for 30 seconds to form a homogeneous solution, then cooled to room temperature. The solvent was concentrated in vacuo to 4 ml, diluted with ethyl acetate (20 ml), washed (H$_2$O and brine) and dried over Na$_2$SO$_4$ (anhydrous). Evaporation of the solvent in vacuo yielded 75.5 mg (74%) of synthetically pure material as a red powder: TLC (silica gel) 85 CHCl$_3$/15 MeOH/0.5 HOAc, Rf 0.37; $^1$H NMR (300 MHz, acetone.d$_6$/TMS) δ 2.39 (3H, s, —COCH$_3$), 3.88 (2H, s, —COCH$_2$S—), 6.61 (2H, dd, J=8.6, 2.3, Hz), 6.68 (2H, s), 6.72 (2H, t), 7.21 (1H, d, J=8.3 Hz), 7.89 (1H, dd, J=2.1, 8.3 Hz), 8.38 (1H, dd, J=1.6 Hz).

EXAMPLE 10

Preparation of 5-(2-Mercaptoacetamido)fluorescein (5-Fl)—NHCOCH$_2$SH (Fluorescein III)

A 15 ml round-bottomed flask was charged with 5-(2-thioacetyl)acetamido)fluorescein (185 mg, 0.40 mM) and methanol (4.5 ml). Sodium borohydride (80.2 mg, 2.12 mM) was added in 4 portions at room temperature. The solution was brought to reflux briefly (15 second). By TLC (15 MeOH/85 CHCl$_3$/0.5 HOAc), no starting material remained. Acidification to pH 5 (6N HCl) and concentration of the solvent yielded the product as a red powder: TLC (silica gel) 85 CHCl$_3$/15 MeOH/0.5 HOAc, Rf 0.25 (silica gel) 80 CHCl$_3$/20 MeOH, Rf 0.33; $^1$H NMR (300 MHz, DMSO/TMS/2 drops TFA) δ 3.91 (2H, s, —COCH$_2$S—), 6.76 (2H, m), 6.89 (4H, m), 7.27 (1H, d), 7.98 (1H, m), 8.47 (1H, d).

Reaction of fluorescein III with ligands bound to commercially available linkers, such as SMCC, provides labeled reagents useful in the method of the invention. Sulfhydryl groups may be converted to the disulfide through activation with, for example, pyridyl derivatives.

We claim:

1. In a method for the determination of analyte in a sample by means of a specific binding assay, said assay comprising the step of measuring the presence or amount of analyte by detecting or quantitating a fluorescent label present in one of the phases of a two-phase system, the improvement wherein said label is supplied as a compound of the formula:

(4-Fl)—NHCOCR$_2$XL'—Y' or
(5-Fl)—NHCOCR$_2$XL'—Y' wherein
4-Fl and 5-Fl represent a fluoroscein residue or a substituted fluorescein residue conjugated to the adjacent NH through the 4 or 5 position of the fluorescein nucleus respectively;
each R is independently H or lower alkyl (1–4C);
X is —S—S—(CH$_2$)$_n$—, wherein n is 1–4;
L' is the residue of L, wherein L is a functional group capable of forming a covalent bond, L being selected from the group consisting of carboxyl, sulfhydryl, amino, halomethyl, epoxide, aldehyde, hydroxy, derivatized carboxyl and vinyl; and
Y' is the residue of Y, wherein Y is a biological ligand or a biological ligand conjugated to linker wherein the linker is capable of reactivity with L.

2. The method of claim 1 wherein Fl is fluorescein or eosin.

3. The method of claim 1 wherein each R is H.

4. The method of claim 1 wherein Y' is a protein residue or a protein residue conjugated to a linker.

5. The method of claim 4 wherein the protein residue is an immunoglobulin or an immunoreactive fragment thereof.

6. A compound useful as a labeling reagent in a specific binding assay, which has the formula:

(4-Fl)—NHCOCR$_2$XL'—Y' or
(5-Fl)—NHCOCR$_2$XL'—Y' wherein
4-Fl and 5-Fl represent a fluoroscein residue or a substituted fluorescein residue conjugated to the adjacent NH through the 4 or 5 position of the fluorescein nucleus respectively;
each R is independently H or lower alkyl (1–4C);
X is —S—S—(CH$_2$)$_n$—, wherein n is 1–4;
L' is the residue of L, wherein L is a functional group capable of forming a covalent bond, L being selected from the group consisting of carboxyl, sulfhydryl, amino, halomethyl, epoxide, aldehyde, hydroxy, derivatized carboxyl annd vinyl; and
Y' is the residue of Y, wherein Y is a biological ligand or a biological ligand conjugated to linker wherein the linker is capable of reactivity with L.

7. The compound of claim 6 wherein Fl is fluorescein or eosin.

8. The compound of claim 6 wherein each R is H.

9. The compound of claim 6 wherein Y' is a protein residue or a protein residue conjugated to a linker.

10. The compound of claim 9 wherein the protein residue is an immunoglobulin or an immunoreactive fragment thereof.

11. A kit for the conduct of a specific binding assay which comprises the compound of claim 6 and additional reagents required for the conduct of the assay along with instructions therefor.

* * * * *